United States Patent
Okada et al.

(10) Patent No.: US 7,150,718 B2
(45) Date of Patent: Dec. 19, 2006

(54) SLEEP STATE ESTIMATION DEVICE AND PROGRAM PRODUCT FOR PROVIDING A COMPUTER WITH A SLEEP STATE ESTIMATION FUNCTION

(75) Inventors: Shima Okada, Osaka (JP); Takeshi Minamiura, Osaka (JP); Hidetaka Sakai, Katano (JP); Yasushi Yamamoto, Hirakata (JP); Yoshihisa Fujiwara, Uji (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 10/961,679

(22) Filed: Oct. 12, 2004

(65) Prior Publication Data
US 2005/0080349 A1 Apr. 14, 2005

(30) Foreign Application Priority Data
Oct. 14, 2003 (JP) .............................. 2003-354219

(51) Int. Cl.
*A61B 5/08* (2006.01)
(52) U.S. Cl. ...................................... 600/538; 600/529
(58) Field of Classification Search ...................... None
See application file for complete search history.

(56) References Cited

U.S. PATENT DOCUMENTS

| | | | |
|---|---|---|---|
| 4,776,345 A | 10/1988 | Cohen et al. | |
| 5,101,831 A * | 4/1992 | Koyama et al. | 600/500 |
| 5,846,206 A * | 12/1998 | Bader | 600/534 |
| 6,015,388 A | 1/2000 | Sackner et al. | |
| 6,280,392 B1 * | 8/2001 | Yoshimi et al. | 600/534 |
| 6,547,743 B1 | 4/2003 | Brydon | |
| 6,579,233 B1 | 6/2003 | Hursh | |
| 2002/0029000 A1 * | 3/2002 | Ohsaki et al. | 600/500 |
| 2004/0103475 A1 * | 6/2004 | Ogawa et al. | 5/613 |

FOREIGN PATENT DOCUMENTS

| | | | |
|---|---|---|---|
| JP | 9-294731 | 11/1997 | |
| JP | 2000-325315 | * 5/2000 | 600/529 |
| JP | 2003-260040 | 9/2003 | |
| JP | 2004-89267 | 3/2004 | |

OTHER PUBLICATIONS

Watanabe, Takashi, et al. "Estimation of the Sleep Stages from the Bio-Data Non-Invasively Measured in the Sleep" SICE, vol. 38, No. 7, 581/589, 2002, pp. 39-47.

* cited by examiner

*Primary Examiner*—Robert L. Nasser
(74) *Attorney, Agent, or Firm*—McDermott Will & Emery LLP (57) ABSTRACT

An object of the present invention is to provide a sleep state estimation device capable of estimating a sleep state (deep sleep, light sleep) in real time with relative simplicity. Voltage variations resulting from human respiratory movement are measured for each given period to calculate from the measurement results positive voltage peak values and time intervals between adjacent peaks. The obtained peak values and peak intervals are used to calculate a mean peak interval value A, a coefficient of variation B based on dispersion of the peak intervals, and a coefficient of variation C based on the peak values. The sleep state in this period is estimated from the calculation results. More specifically, referring to FIG. 5, the sleep state is estimated as a "wakeful state" or a "hypnagogic state" by checking whether the mean value A is larger or smaller than a threshold a and whether the coefficient of variation C is larger or smaller than a threshold c (S105) whereas the sleep state is estimated as the "hypnagogic state", "light sleep" or "deep sleep" by checking whether the coefficient of variation B is larger or smaller than a threshold b and whether the coefficient of variation C is larger or smaller than the threshold c (S109, S113, S116, S117).

12 Claims, 9 Drawing Sheets

SLEEP STATE ESTIMATION DEVICE AND PROGRAM PRODUCT FOR PROVIDING A COMPUTER WITH A SLEEP STATE ESTIMATION FUNCTION

BACKGROUND OF THE INVENTION

1. Field of the Invention

The present invention relates to a sleep state estimation device which estimates a sleep state based on vital signs information, and to a program product for executing a sleep state estimation function.

2. Description of the Related Art

Recently heightened health consciousness among people has created a desire to manage their health by day-to-day sleep control in their household. Sleep is divided by type into REM sleep which is a light sleep and non-REM (NREM) sleep which is a deep sleep. A finer sleep classification is Sleep Stage. Sleep Stage is an international standard consisting of "REM sleep", "Sleep Stages 1, 2, 3 and 4" and "wakefulness", which are judged from electroencephalogram (EEG), ocular movement, and electric potentials generated by movement of jaw muscles. "Sleep Stages 1, 2, 3 and 4" correspond to NREM sleep during which a person sleeps deep. Polysomography is a known method to judge the sleep state. According to this method, the aforementioned EEG, ocular movement, and electric potentials generated by movement of jaw muscles are detected to judge from the waveforms detected which sleep stage a subject is in.

Other known sleep stage estimation methods than polysomography involve applying the neural network theory, the chaos theory, or the like to measurements of respiration rate, heart rate, and body movement. Those methods are described in JP09-294731 A and on pages 581–589 in Vol. 38, No. 7 of collected papers published by The Society of Instrument and Control Engineers in 2002.

The above-described sleep stage estimation according to prior art places particular emphasis on variations and intervals of heart rate out of respiration rate, heart rate, and body movement information measured. In general, electrocardiogram (ECG) is used to measure heart rate with precision. Measurement by ECG, however, has a drawback in that plural electrodes have to be attached directly to the skin of a subject, restraining the subject with their codes which are connected to ECG equipment. On the other hand, a non-restrictive sensor can only catch minute heart rate signals, which are also full of noises from other elements than heartbeat. Non-restrictive measurement therefore needs FFT and filter computation processing for frequency analysis as well as signal amplification processing, which complicate the measurement process.

SUMMARY OF THE INVENTION

The present invention has been made in view of the above, and an object of the present invention is therefore to provide a sleep state estimation device capable of estimating a sleep state in real time with relative simplicity. To attain this object, the present invention focuses on the relation between respiratory movement and sleep state, and estimates the sleep state (deep sleep, light sleep) based on regular or irregular variations of respiratory movement.

According to a first aspect of the present invention, a sleep state estimation device for estimating a sleep state is characterized by including: vital signs information processing means for extracting respiratory signals from output signals of a vital signs information sensor; and sleep state estimating means for estimating the sleep state based on the respiratory signals outputted by the vital signs information processing means.

In the sleep state estimation device according to the first aspect of the present invention, the sleep state estimating means includes: peak calculating means for calculating respiratory signal peak values in a given period from the respiratory signals outputted by the vital signs information processing means; and peak interval calculating means for calculating respiratory signal peak intervals in the given period from the respiratory signals, in which the sleep state estimating means estimates the sleep state based on the peak values and the peak intervals.

More specifically, in the sleep state estimation device, the sleep state estimating means further includes: first coefficient of variation calculating means for calculating, from the peak intervals obtained by the peak interval calculating means, a first coefficient of variation which is based on dispersion of the peak intervals; and second coefficient of variation calculating means for calculating, from the peak values obtained by the peak calculating means, a second coefficient of variation which is based on dispersion of the peak values, in which the sleep state estimating means estimates the sleep state by comparing the first coefficient of variation and the second coefficient of variation against given thresholds.

Further, in the sleep state estimation device, the sleep state estimating means further includes: mean peak interval calculating means for calculating, from the peak intervals obtained by the peak interval calculating means, a mean value of the peak intervals; and second coefficient of variation calculating means for calculating, from the peak values obtained by the peak calculating means, a second coefficient of variation which is based on dispersion of the peak values, in which the sleep state estimating means estimates the sleep state by comparing the mean peak interval value and the second coefficient of variation against given thresholds.

In addition, in the sleep state estimation device, the sleep state estimating means further includes: first coefficient of variation calculating means for calculating, from the peak intervals obtained by the peak interval calculating means, a first coefficient of variation which is based on dispersion of the peak intervals; second coefficient of variation calculating means for calculating, from the peak values obtained by the peak calculating means, a second coefficient of variation which is based on dispersion of the peak values; and mean peak interval calculating means for calculating, from the peak intervals obtained by the peak interval calculating means, the mean value of the peak intervals, in which the sleep state estimating means estimates the sleep state by comparing the first coefficient of variation and the second coefficient of variation against given thresholds, and by comparing the mean peak interval value and the second coefficient of variation against given thresholds.

The present invention can also take the form of a program product which provides a computer with a sleep state estimation function. In this case, the program product is characterized by including a vital signs information processing step of extracting respiratory signals from output signals of a vital signs information sensor and a sleep state estimating step of estimating a sleep state based on the respiratory signals extracted in the vital signs information processing step.

In the program product of the above-mentioned aspect, the sleep state estimating step includes: a peak calculating step of calculating respiratory signal peak values in a given period from the respiratory signals extracted in the vital signs information processing step; and a peak interval calculating step of calculating respiratory signal peak intervals in the given period from the respiratory signals, in which the sleep state is estimated based on the peak values and the peak intervals in the sleep state estimating step.

More specifically, in the program product, the sleep state estimating step further includes: a first coefficient of variation calculating step of calculating, from the peak intervals obtained in the peak interval calculating step, a first coefficient of variation which is based on dispersion of the peak intervals; and a second coefficient of variation calculating step of calculating, from the peak values obtained in the peak calculating step, a second coefficient of variation which is based on dispersion of the peak values, in which the sleep state is estimated by comparing the first coefficient of variation and the second coefficient of variation against given thresholds in the sleep state estimating step.

Further, in the program product, the sleep state estimating step further includes: a mean peak interval calculating step of calculating, from the peak intervals obtained in the peak interval calculating step, a mean value of the peak intervals; and a second coefficient of variation calculating step of calculating, from the peak values obtained in the peak calculating step, a second coefficient of variation which is based on dispersion of the peak values, in which the sleep state is estimated by comparing the mean peak interval value and the second coefficient of variation against given thresholds in the sleep state estimating step.

In addition, in the program product, the sleep state estimating step further includes: a first coefficient of variation calculating step of calculating, from the peak intervals obtained in the peak interval calculating step, a first coefficient of variation which is based on dispersion of the peak intervals; a second coefficient of variation calculating step of calculating, from the peak values obtained in the peak calculating step, a second coefficient of variation which is based on dispersion of the peak values; and a mean peak interval calculating step of calculating, from the peak intervals obtained in the peak interval calculating step, the mean value of the peak intervals, in which the sleep state is estimated by comparing the first coefficient of variation and the second coefficient of variation against given thresholds and by comparing the mean peak interval value and the second coefficient of variation against given thresholds in the sleep state estimating step.

BRIEF DESCRIPTION OF THE DRAWINGS

The aforementioned and other objects and novel features of the present invention will become more apparent from the following description of an embodiment when taken in conjunction with the accompanying drawings in which.

DETAILED DESCRIPTION OF THE PREFERRED EMBODIMENTS

An embodiment of the present invention is described below with reference to the drawings. The following embodiment is merely an example of the present invention, and is not to limit the scope of the invention.

Figure 1:
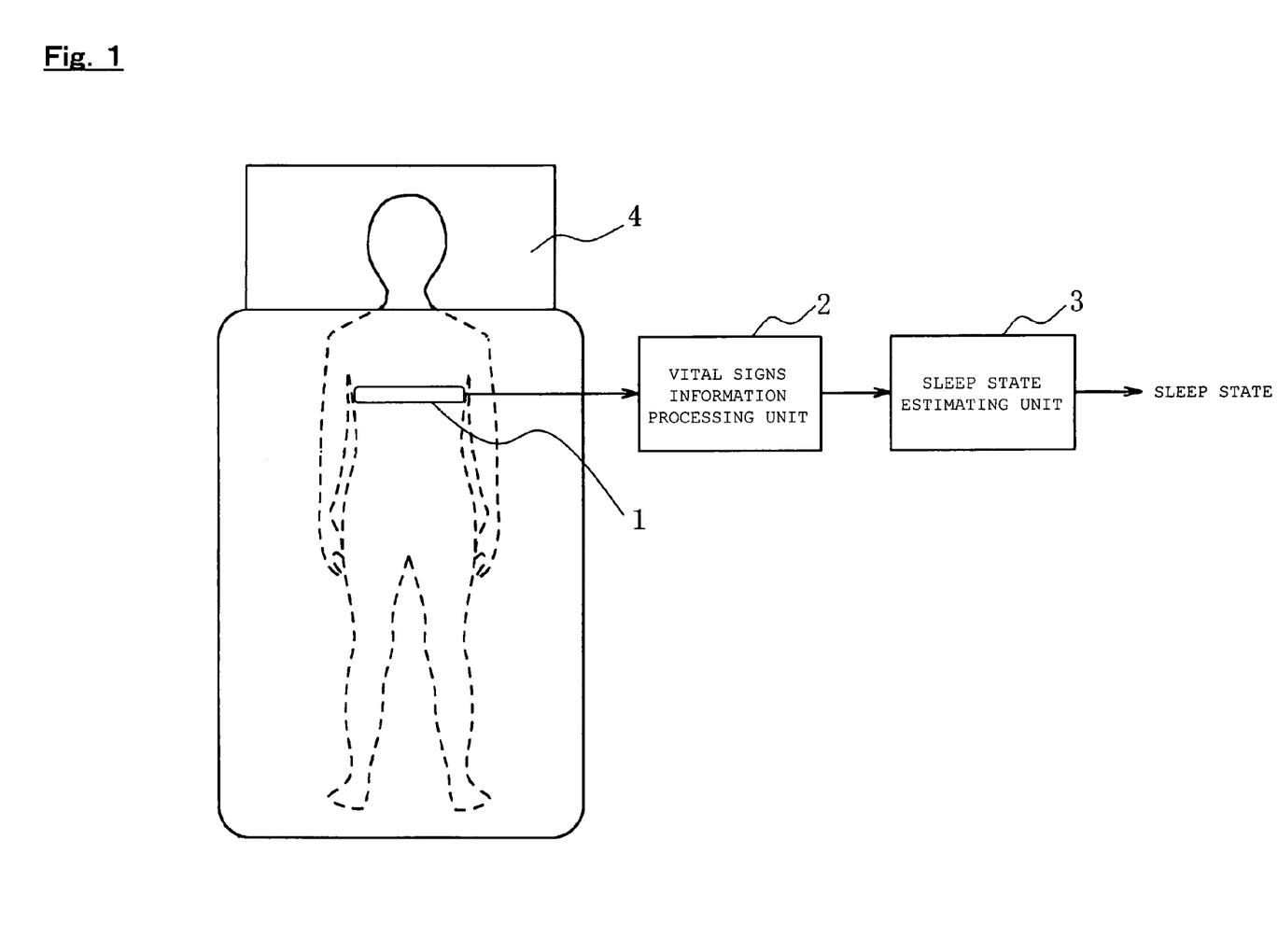
FIG. 1 shows the structure of a sleep state estimation device according to an embodiment of the present invention.

Referring to FIG. 1, a sleep state estimation device according to the present embodiment is composed of a respiratory band 1, which is one of vital signs information sensors, a vital signs information processing unit 2, and a sleep state estimating unit 3. In FIG. 1, a person is lying on a mattress 4 with the respiratory band 1 attached to his/her upper body.

Figure 2:
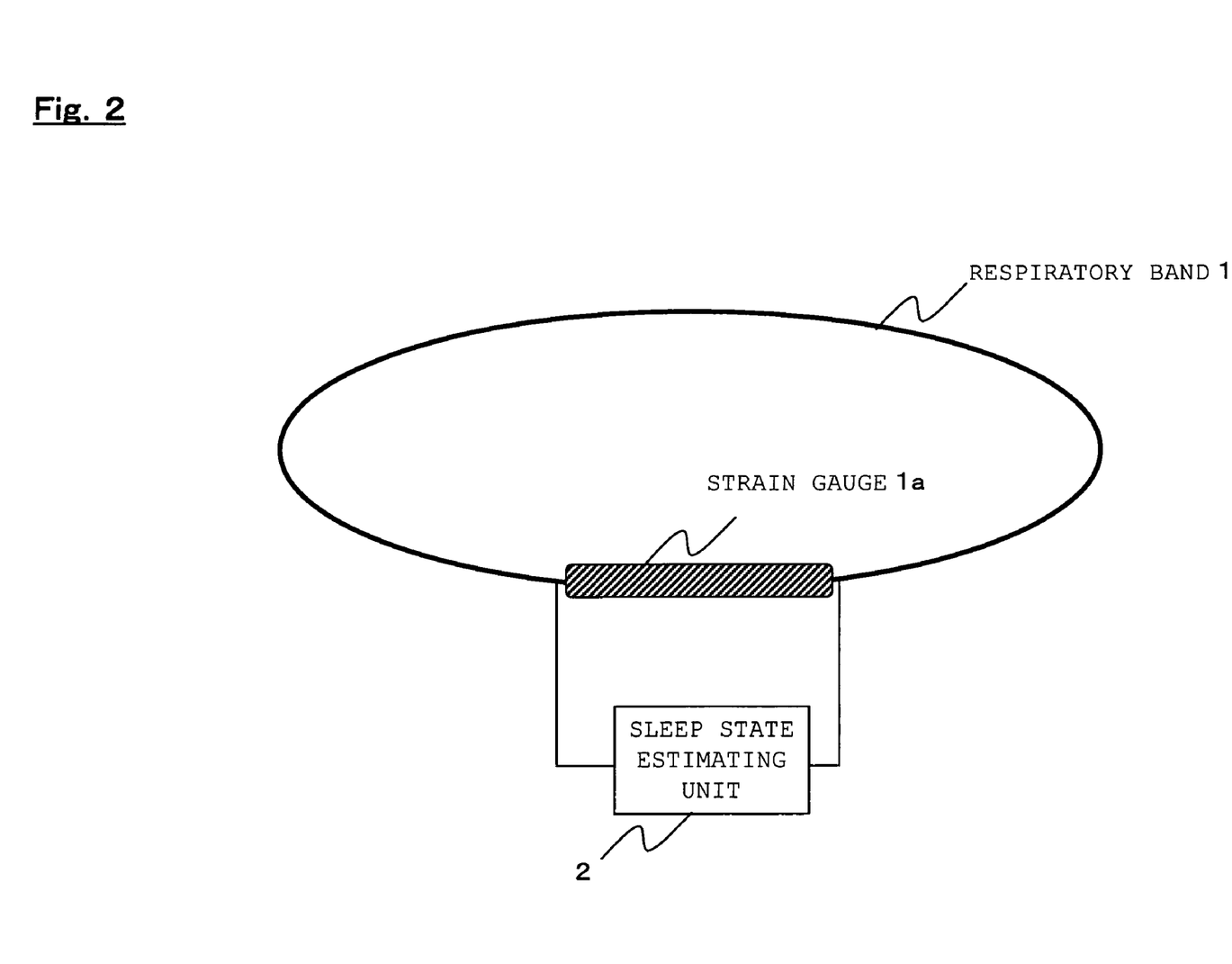
FIG. 2 shows a respiratory band which is one of vital signs information sensors according to the embodiment.

The respiratory band 1 is, as shown in FIG. 2, an elastic band having a strain gauge 1a. The strain gauge 1a is made from, for example, a carbon tube or a zinc sulfate solution tube. The respiratory band 1 is wound around the chest or abdominal area of the subject, and respiratory movement of the subject expands and contracts the strain gauge 1a, thereby changing the electric resistance of the gauge.

The vital signs information processing unit 2 applies a fixed voltage to both ends of the strain gauge 1a and measures a change in voltage of the strain gauge 1a due to a resistance shift as a change caused by respiratory movement of the subject.

Figure 3:
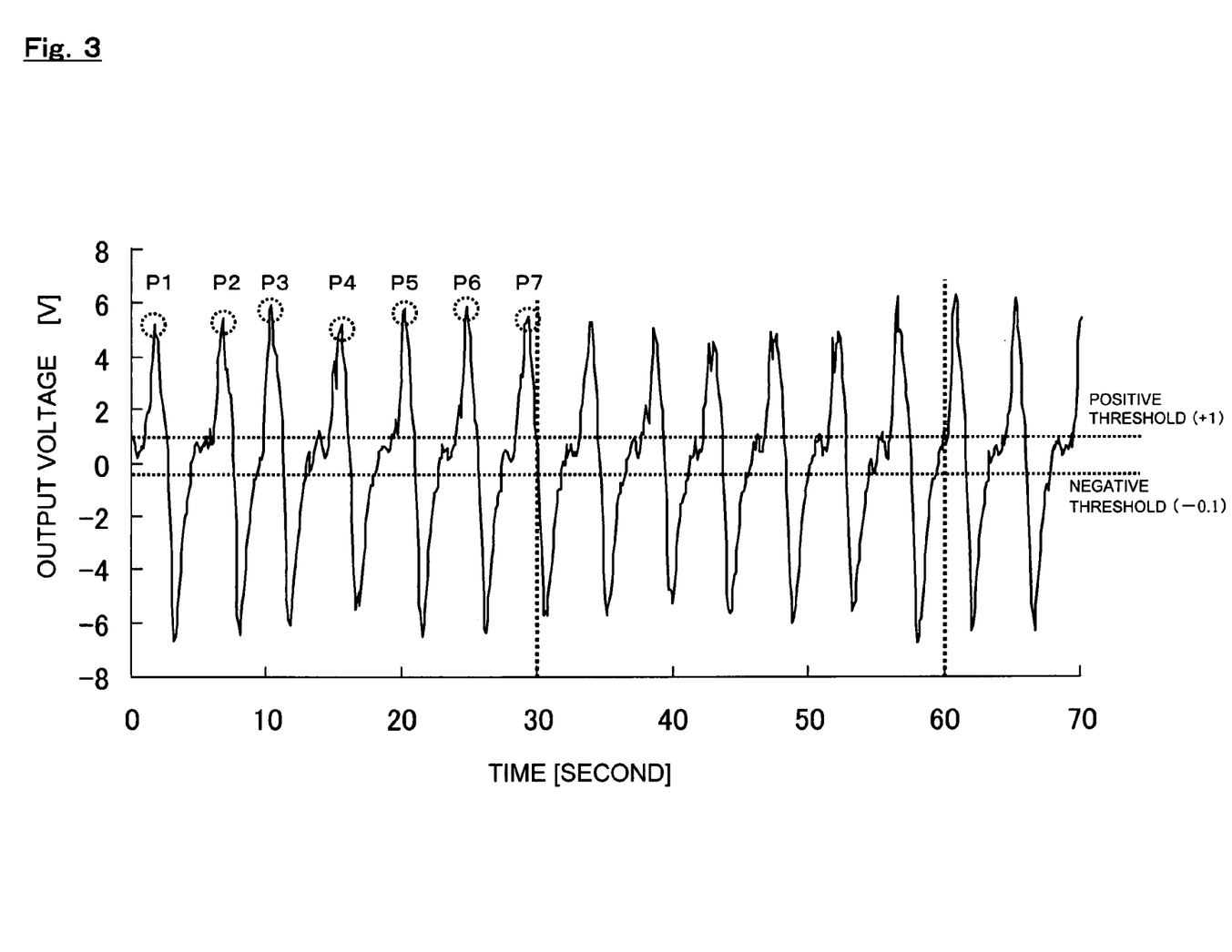
FIG. 3 shows respiratory signals extracted by a vital signs information processing unit according to the embodiment.

FIG. 3 shows voltage changes which are due to subject's respiratory movement and measured by the vital signs information processing unit 2. In FIG. 3, an axis of abscissa represents measurement time (t) whereas an axis of ordinate represents voltage (v).

The sleep state estimating unit 3 samples the voltage changes measured by the vital signs information processing unit 2 at a sampling frequency of 10 Hz to digitize the measurement. The sleep state estimating unit 3 then splits the digitized data by time into 30-second sections (epochs), and calculates positive voltage peak values and peak intervals between adjacent peak values for each 30-second epoch as follows: the maximum value in a period after the measured voltage change data exceeds a given positive threshold until the data reaches a given negative threshold is calculated as a positive voltage peak value. A positive peak interval value is the time counted from the obtained positive peak value to the arrival of the next positive peak value.

With the negative threshold thus set, erroneous detection of a positive peak value can be prevented. In FIG. 3, the epoch whose time count is 0 through 30 seconds has seven positive peak points (P1 through P7), and a value 1 is set as the positive threshold whereas a value −0.1 is set as the negative threshold. The sleep state estimating unit 3 calculates the time interval (peak interval value) between each of the seven peak points (P1 through P7) and their respective adjacent peak points in the manner described above.

Next, the sleep state estimating unit 3 obtains an mean value A of the positive voltage peak interval values calculated for the 30-second epochs, a coefficient of variation B based on dispersion of the peak interval values, and a coefficient of variation C based on dispersion of the positive voltage peak values. The sleep state estimating unit 3 then compares the obtained mean positive voltage peak interval value A, coefficient of variation B and coefficient of variation C against sleep state estimation thresholds a, b and c, respectively, to thereby estimate which sleep state of "wakeful state", "hypnagogic state", "deep sleep" and "light sleep" the subject is in.

In the "wakeful state", the subject is awake. The "hypnagogic state" refers to the state which immediately follows the "wakeful state" and in which the subject has just fallen asleep. "Light sleep" refers to a deeper sleep than in the "hypnagogic state". "hypnagogic state" is included in "Light sleep", but it is so extra that it is distinguished from "Light sleep". In "deep sleep", the subject's sleep is deeper than in the "light sleep" state and the "deep sleep" state refers to the deepest sleep state.

The sleep states estimated by the sleep state estimation device of this embodiment correspond to the internationally standardized sleep stage definitions as follows:

The "wakeful state" in estimation of this embodiment corresponds to "wakefulness" in sleep stage scoring. The "hypnagogic state" in estimation of this embodiment corresponds to "Sleep Stages 1 and 2 that appear first after a person falls asleep" in sleep stage scoring. "Light sleep" in estimation of this embodiment corresponds to "REM and Sleep Stages 1 and 2" in sleep stage scoring, except "Sleep Stages 1 and 2 that appear first after a person falls asleep". "Deep sleep" in estimation of this embodiment corresponds to "Sleep Stages 3 and 4" in sleep stage scoring.

Figure 4:
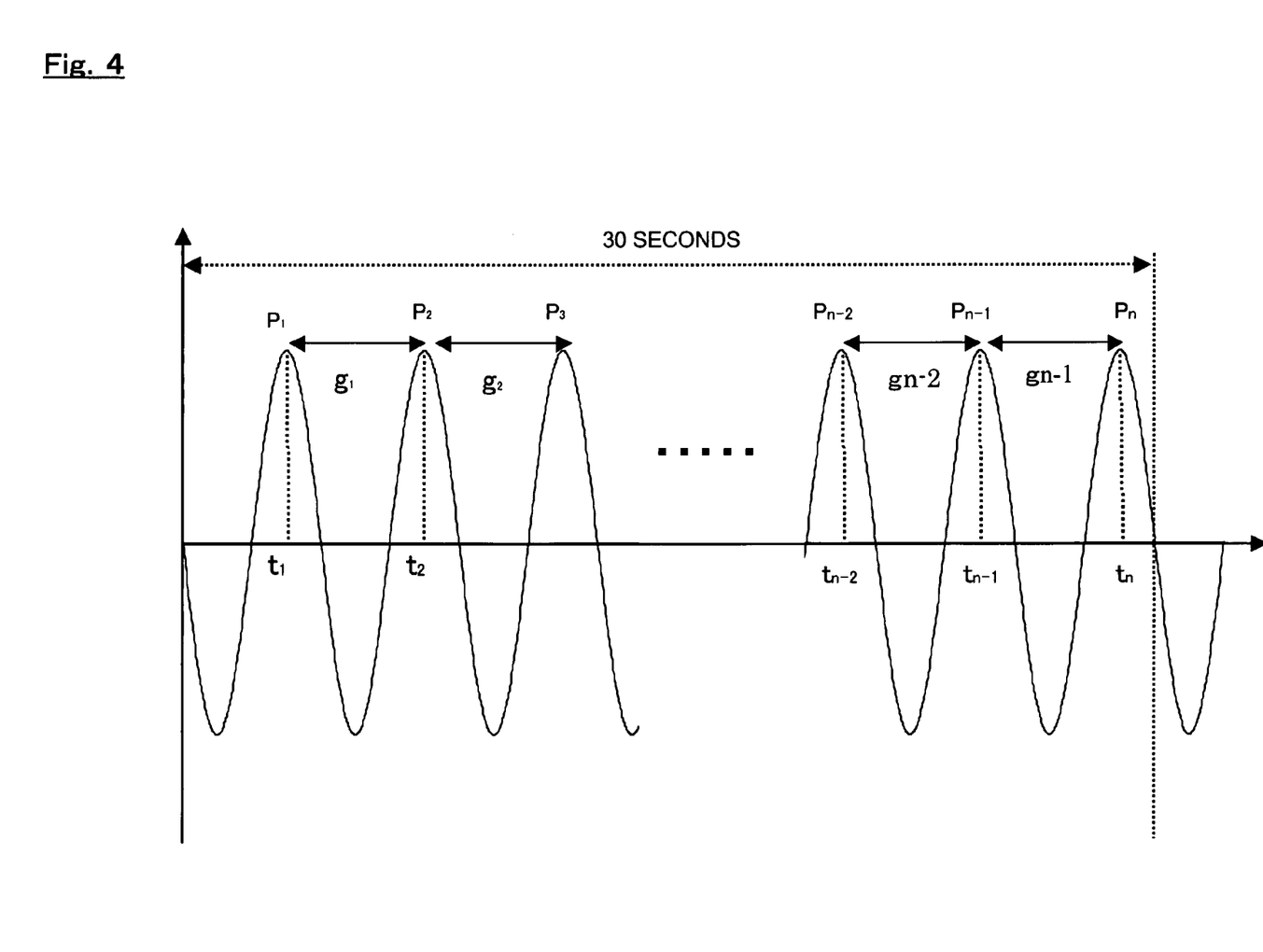
FIG. 4 shows model waveforms of respiratory signals extracted by the vital signs information processing unit according to the embodiment.

A description is given below with reference to FIG. 4 on how to calculate the mean peak interval value A, the coefficient of variation B, and the coefficient of variation C. FIG. 4 is a model diagram of voltage changes measured in 30 seconds by the vital signs information processing unit 2 which is created for convenience in explaining calculation methods of the mean positive voltage peak interval value A, the coefficient of variation B, and the coefficient of variation C.

In FIG. 4, Pi (i=1, 2, . . . n) represents a positive voltage peak value, ti (i=1, 2, . . . n) represents a time at which the voltage peaks, and gi (i=1, 2, . . . n−1) represents a positive voltage peak interval.

The peak interval gi is calculated by the following expression:

$$g_i = t_{i+1} - t_i \ (i=1, 2, \ldots n-1)$$

The mean positive voltage peak interval value A is calculated by the following expression:

$$A = \frac{\sum_{i=1}^{n-1} g_i}{n-1}$$

The average of positive voltage peak values is calculated by the following expression:

$$\overline{P} = \frac{\sum_{i=1}^{n} P_i}{n}$$

The coefficient of variation B is a value obtained by dividing dispersion of positive voltage peak intervals by the mean positive voltage peak interval value A, and therefore is calculated by the following expression:

$$B = \frac{\sum_{i=1}^{n-1} (A - g_i)^2}{n-1} \Big/ A$$

The coefficient of variation C is a value obtained by dividing dispersion of positive voltage peak values by the average of positive voltage peak values, and therefore is calculated by the following expression:

$$C = \frac{\sum_{i=1}^{n} (\overline{P} - P_i)^2}{n-1} \Big/ \overline{P}$$

The sleep state estimating unit 3 estimates the sleep state from the mean positive voltage peak interval value A, the coefficient of variation B, and the coefficient of variation C which are calculated using the above expressions.

A description is given below with reference to FIG. 5 on how the sleep state estimating unit 3 estimates the sleep state.

Figure 5:
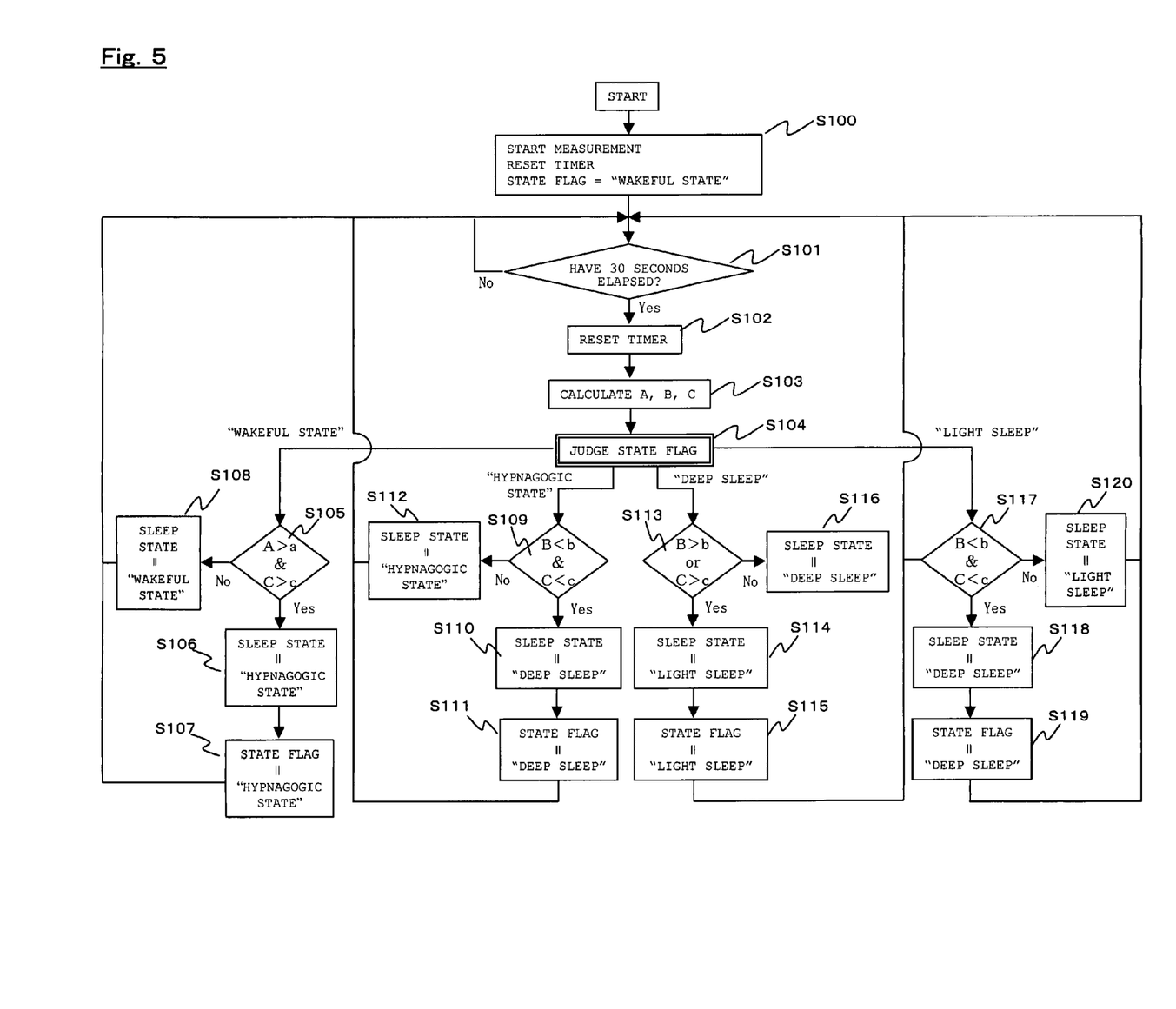
FIG. 5 is a flow chart for sleep state estimation according to the embodiment.

Referring to FIG. 5, a timer is reset in Step S100 to count up measurement time and to have the vital signs information processing unit 2 start measuring voltage changes caused by respiratory movement of the subject. At this point, "wakeful state" is set as the initial value of a state flag. The state flag indicates the sleep state according to voltage measurement data of the preceding epoch.

In Step S101, the sleep state estimating unit 3 judges whether or not 30 seconds have elapsed since the timer is reset. If it is after 30 seconds, the process proceeds to Step S102, where the timer is reset and starts counting measurement time again.

In Step S103, the sleep state estimating unit 3 uses the above-described calculation methods to calculate the mean positive voltage peak interval value A, the coefficient of variation B, and the coefficient of variation C from the measurement results on voltage changes in 30 seconds.

In Step S104, the value of the state flag is judged.

When it is judged in Step S104 that the state flag indicates the "wakeful state", the process proceeds to Step S105 whereas the next step is Step S109 when the state flag indicates the "hypnagogic state", Step S113 when the state flag indicates "deep sleep", and Step S117 when the state flag indicates "light sleep".

In Step S105, the sleep state estimating unit 3 judges whether or not the mean positive voltage peak interval value A is larger than the given threshold a and the coefficient of variation C is larger than the given threshold c. When the result is "Yes", the process proceeds to Step S106 whereas Step S108 is processed next in the case where the result is "No".

In Step S106, the sleep state is estimated as the "hypnagogic state" and the process proceeds to Step S107.

In Step S107, the state flag is set to the "hypnagogic state" and the process is returned to Step S101.

In Step S108, the sleep state is estimated as the "wakeful state" and the process is returned to Step S101.

In Step S109, the sleep state estimating unit 3 judges whether or not the coefficient of variation B is smaller than the given threshold b and the coefficient of variation C is smaller than the given threshold c. When the result is "Yes", the process proceeds to Step S110 whereas Step S112 is processed next in the case where the result is "No".

In Step S110, the sleep state is estimated as "deep sleep" and the process proceeds to Step S111.

In Step S111, the state flag is set to "deep sleep" and the process is returned to Step S101.

In Step S112, the sleep state is estimated as the "hypnagogic state" and the process is returned to Step S101.

In Step S113, the sleep state estimating unit 3 judges whether or not the coefficient of variation B is smaller than the given threshold b and the coefficient of variation C is smaller than the given threshold c. When the result is "Yes", the process proceeds to Step S114 whereas Step S116 is processed next in the case where the result is "No".

In Step S114, the sleep state is estimated as "light sleep" and the process is proceeds Step S115.

In Step S115, the state flag is set to "light sleep" and the process is returned to Step S101.

In Step S116, the sleep state is estimated as "deep sleep" and the process is returned to Step S101.

In Step S117, the sleep state estimating unit 3 judges whether or not the coefficient of variation B is smaller than the given threshold b and the coefficient of variation C is smaller than the given threshold c. When the result is "Yes", the process proceeds to Step S118 whereas Step S120 is processed next in the case where the result is "No".

In Step S118, the sleep state is estimated as "deep sleep" and the process is returned to Step S119.

In Step S119, the state flag is set to "deep sleep" and the process is returned to Step S101.

In Step S120, the sleep state is estimated as "light sleep" and the process is returned to Step S101.

As described above, the sleep state estimating unit 3 then compares the obtained mean positive voltage peak interval value A, coefficient of variation B and coefficient of variation C against sleep state estimation thresholds a, b and c, respectively, to thereby estimate which sleep state of "wakeful state", "hypnagogic state", "deep sleep" and "light sleep" the subject is in.

Figure 6A:
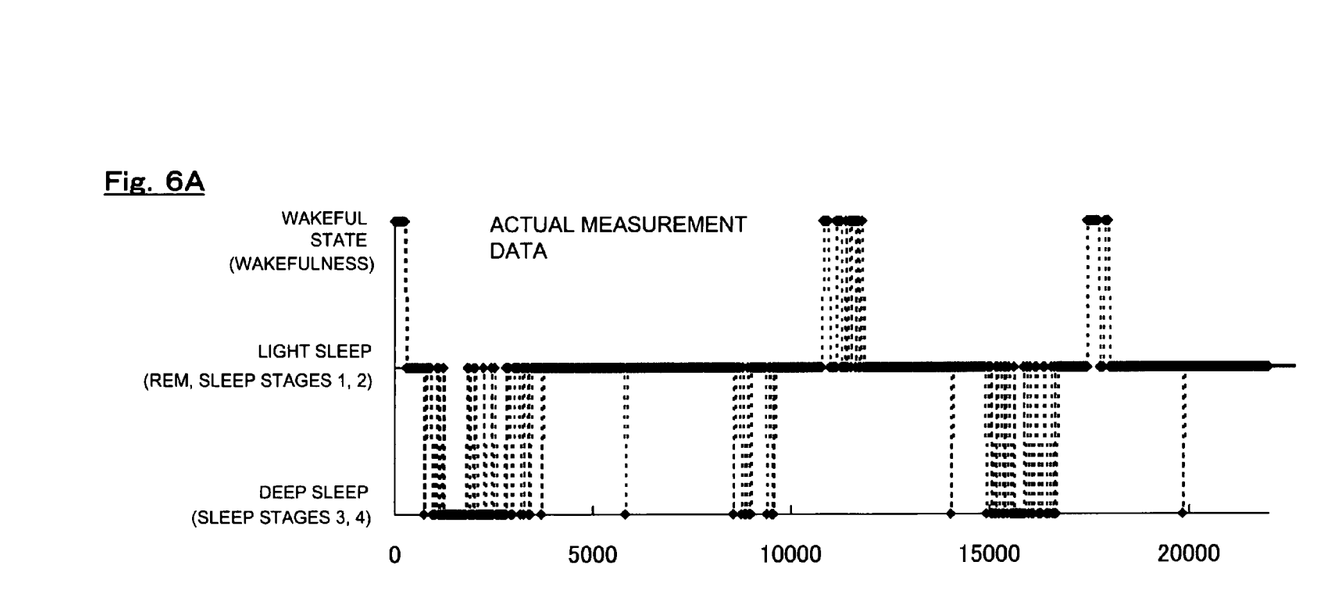
FIGS. 6A and 6B are graphs in which sleep estimation results provided by the sleep state estimation device according to the embodiment are compared with actual sleep stage data measured by polysomography.
Figure 6B:
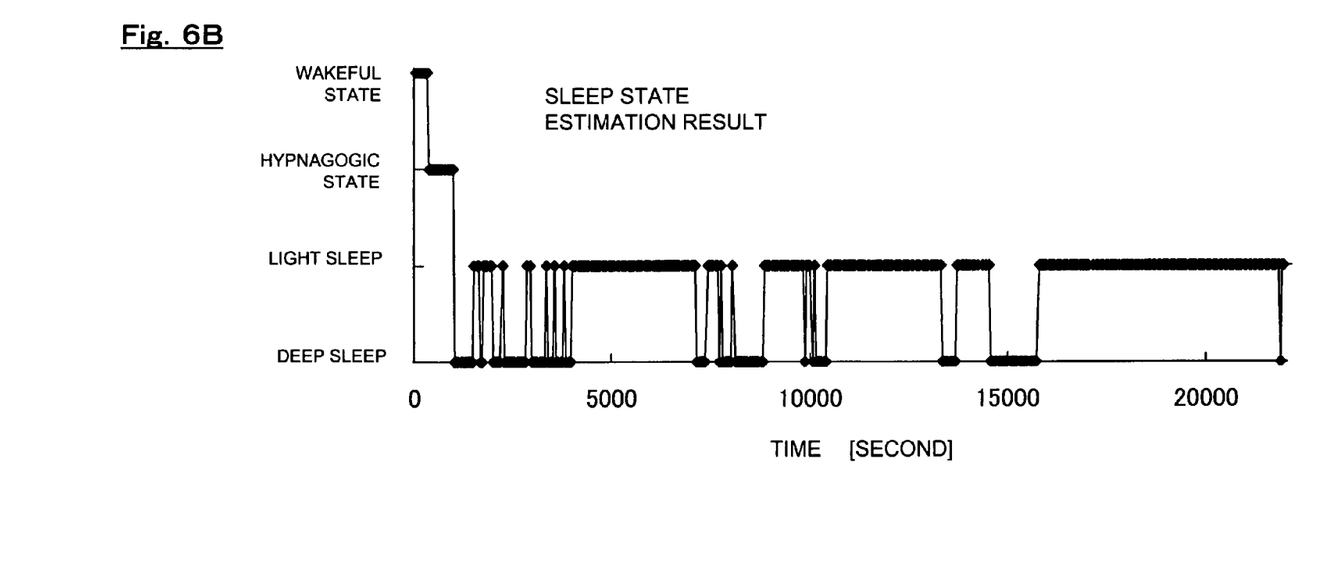

FIGS. 6A and 6B are for comparison of sleep state estimation results on a certain subject by the sleep state estimation device of this embodiment (FIG. 6B) against actually measured sleep stage data on the same subject by polysomography (FIG. 6A). In FIG. 6A, "REM and Sleep Stages 1 and 2" in sleep stage scoring are expressed as "light sleep" and "Sleep Stages 3 and 4" as "deep sleep" for the ease of comparison with the estimation results of FIG. 6B.

In calculating the estimation results of FIG. 6B, the positive and negative thresholds for peak detection which are shown in FIG. 3 are set to 1 and −0.1, respectively. The sleep state estimation thresholds a, b and c shown in FIG. 5 are set to 4.0, 0.08 and 0.08, respectively.

In FIG. 6B, the mean value A of voltage peak interval values within 30 seconds from the start of measurement, the coefficient of variation B based on dispersion of the peak interval values, and the coefficient of variation C based on dispersion of the peak values are 3.14, 0.27404, and 0.24292, respectively.

A comparison between FIGS. 6A and 6B reveals that "light sleep (REM and Sleep Stages 1 and 2)" heading the actual measurement data of FIG. 6A appears at approximately the same time the "hypnagogic state" is estimated by the sleep state estimation device of this embodiment. Also, "light sleep (REM and Sleep Stages 1 and 2)" in the subsequent portion of the actual measurement data substantially coincides with "light sleep" estimated by the sleep state estimation device of this embodiment, and "deep sleep (Sleep Stages 3 and 4)" in actual measurement data substantially coincides with "deep sleep" estimated by the sleep state estimation device of this embodiment. The estimation results provided by the sleep state estimation device of this embodiment and actually measured sleep stage data thus exhibit very similar moves, which shows that this sleep state estimation device has high accuracy.

As proved by the above testing results, this embodiment is capable of estimating the sleep state with high precision by measuring voltage changes that accompany human respiratory movement, obtaining, from the measurement results, positive voltage peak values and peak interval values for each given period, and calculating the mean value A of the peak interval values, the coefficient of variation B based on dispersion of the peak interval values, and the coefficient of variation C based on dispersion of the peak values.

Figure 7:
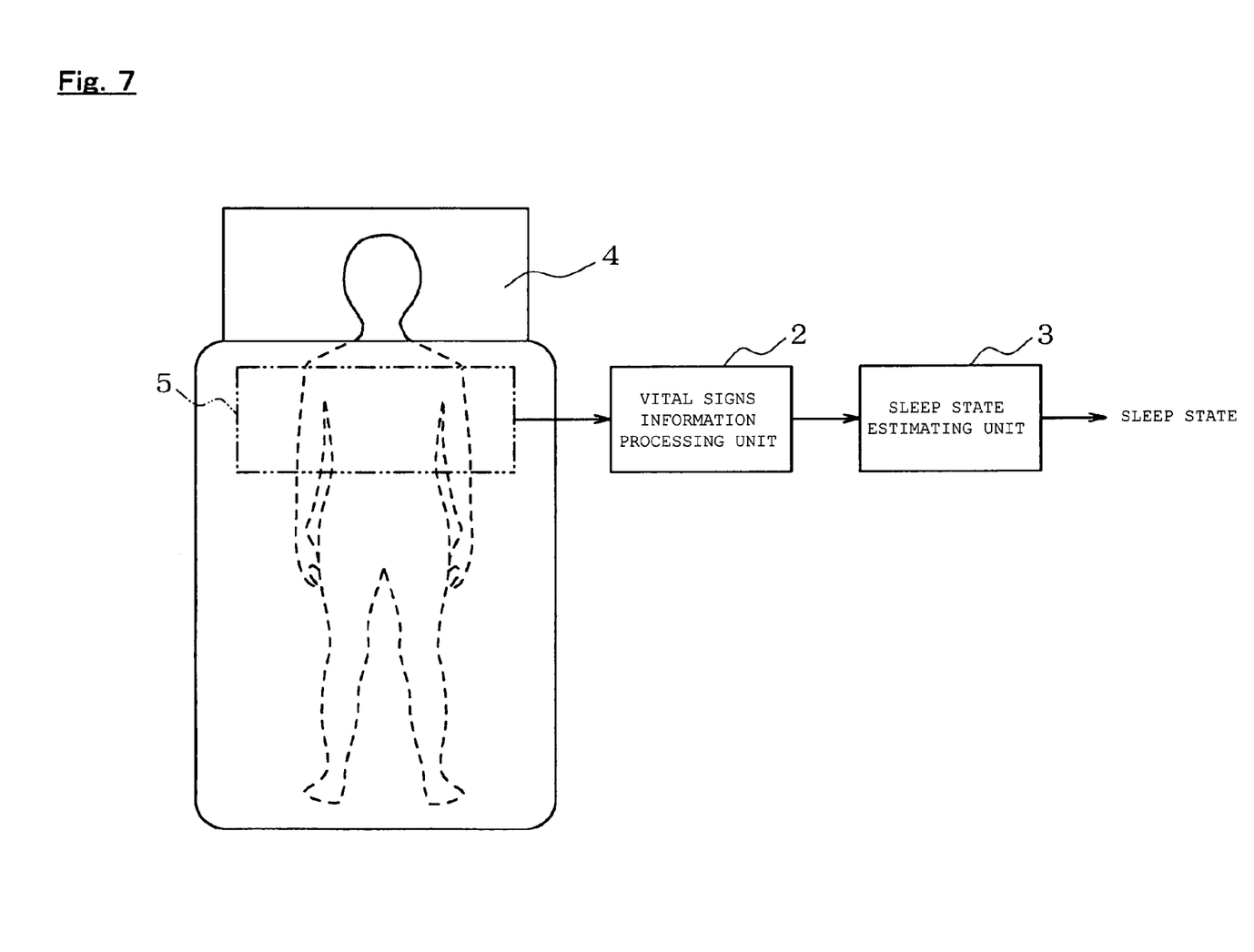
FIG. 7 shows a sleep state estimation device structure for when a sheet-like, electrostatic capacity type, non-restrictive vital signs information sensor is employed.
Figure 8:
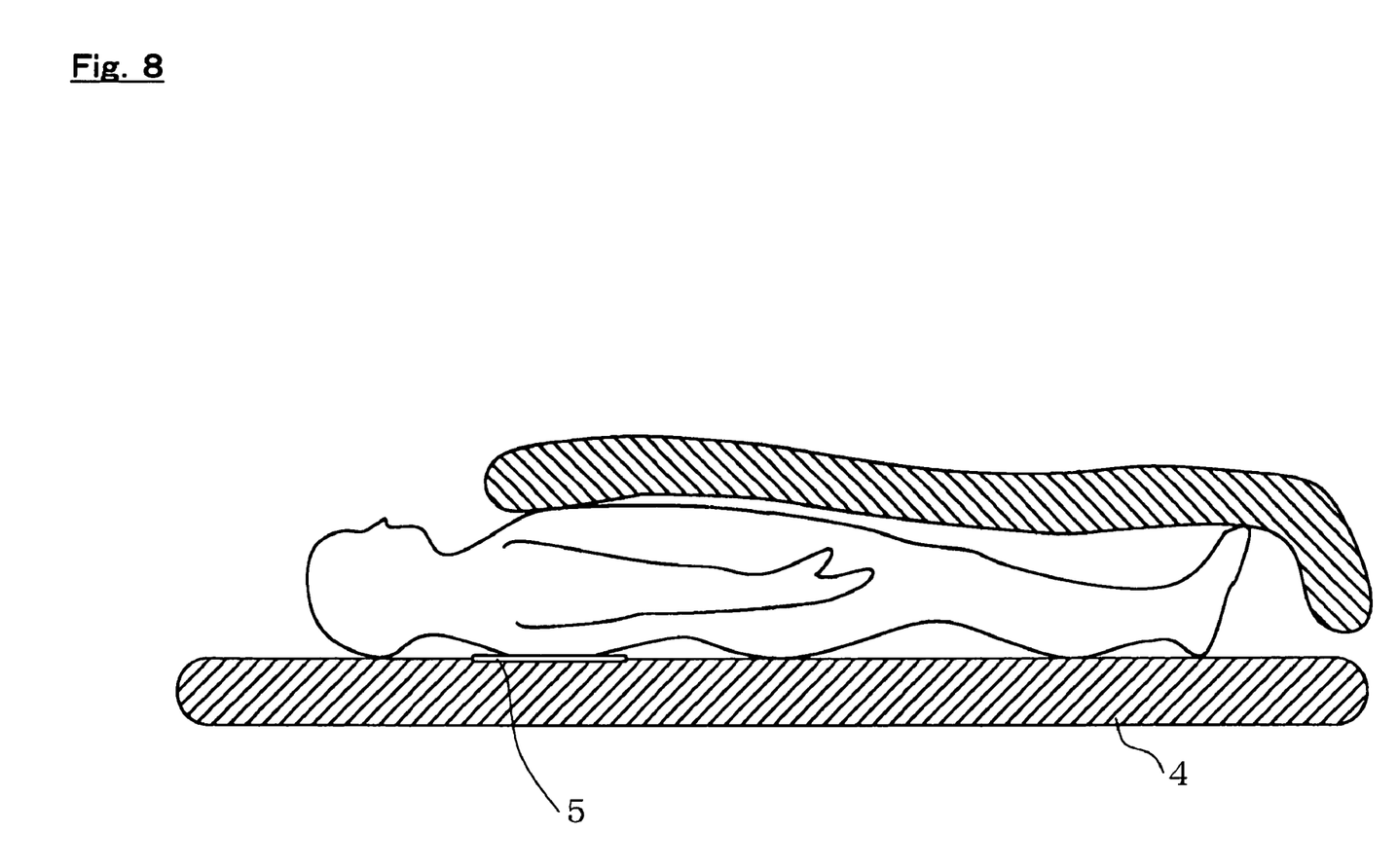
FIG. 8 shows a sleep state estimation device structure for when the sheet-like, electrostatic capacity type, non-restrictive vital signs information sensor is employed.

The above embodiment, in which a respiratory band is used as the vital signs information sensor to measure human respiratory movement and estimate the sleep state from measurement results of the respiratory movement alone, may be modified to employ an alternative vital signs information sensor, for example, a sheet-like, electrostatic capacity type sensor. In this case, a sheet-like, electrostatic capacity type sensor 5 is attached to the mattress 4 as shown in FIGS. 7 and 8. The upper body of the person presses down on the sheet-like, electrostatic capacity type sensor 5, thereby changing the distance between electrodes and accordingly changing the electrostatic capacity between the electrodes. The vital signs information processing unit 2 measures changes in electrostatic capacity between the electrodes of the sheet-like, electrostatic capacity type sensor 5 which are caused by human respiratory movement and body movement.

The sleep state estimating unit 3 in this case extracts, from output signals of the vital signs information processing unit 2, electrostatic capacity variations due to subject's body movement as well as electrostatic capacity variations caused by respiratory movement.

Electrostatic capacity variations resulting from body movement can be used in estimation of whether the subject is awake (the "wakeful state" in sleep state estimation of the present invention) or asleep (other states than the "wakeful state").

Figure 9:
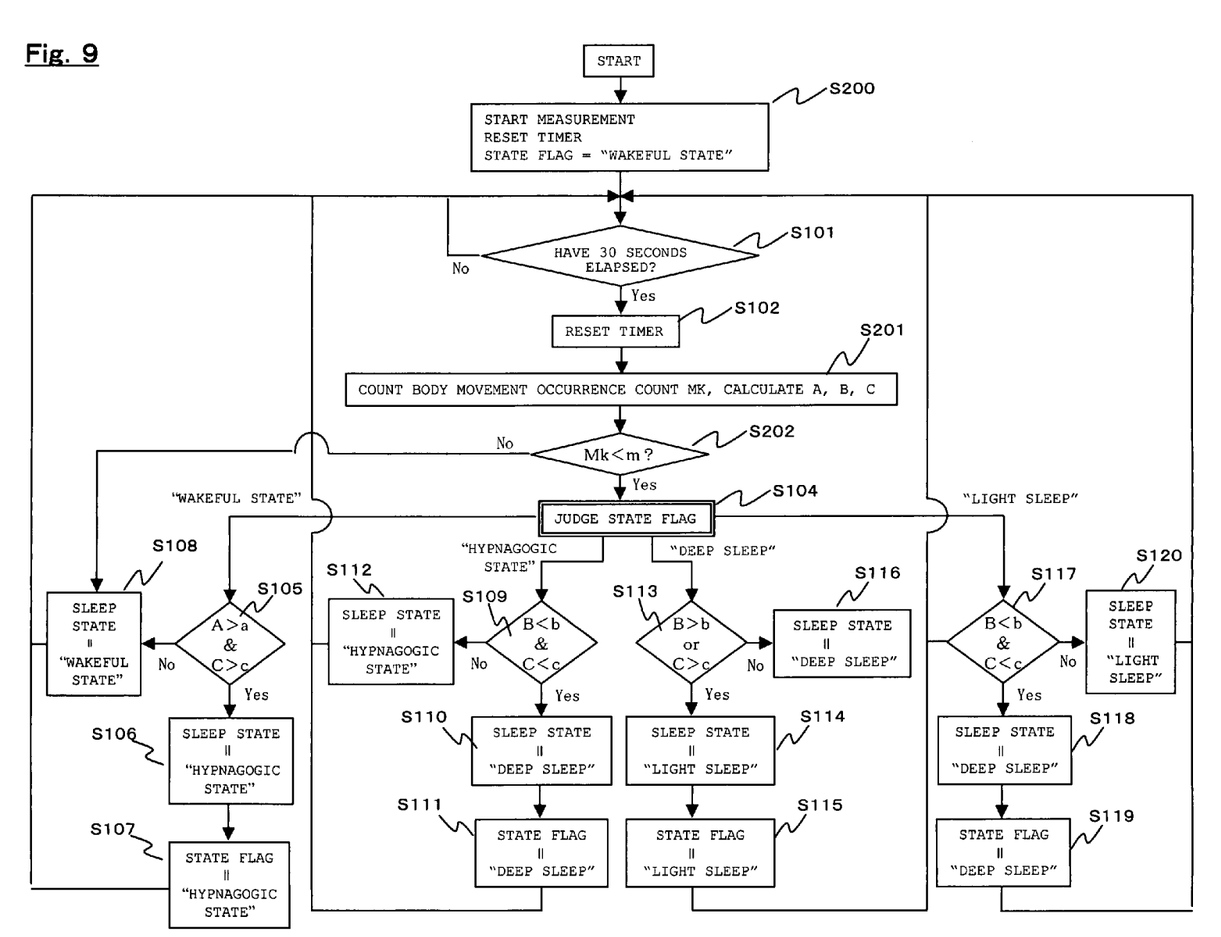
FIG. 9 shows a modification example of the sleep state estimation flow chart which is applied when employing the sheet-like, electrostatic capacity type, non-restrictive vital signs information sensor.

Specifics of how electrostatic capacity variations by body movement are utilized in sleep state estimation are shown in a flow chart of FIG. 9. Of steps in the flowchart of FIG. 9, those identical to the steps in the flow chart of FIG. 4 are denoted by the same symbols. Steps S100 and S103 in the flow chart of FIG. 4 are replaced by Steps S200 and S201, respectively, in the flow chart of FIG. 9. FIG. 9 also has an additional step of Step S202, which is put before Step S104.

Referring to the flow chart of FIG. 9, the vital signs information processing unit 2 measures in Step S200 electrostatic capacity variations of the sheet-like, electrostatic capacity type sensor 5 which are caused by human respiratory movement and body movement.

In Step S201, the sleep state estimating unit 3 separates the electrostatic capacity variations into variations due to body movement and variations due to respiratory movement as follows:

With variations by body movement being larger than variations by respiratory movement, the sleep state estimating unit 3 recognizes variations that are larger than a preset body movement threshold as ones due to body movement, and counts how many times electrostatic capacity variations exceed the body movement threshold as a body movement occurrence count Mk.

When electrostatic capacity variations by body movement are contained in data obtained in an epoch that is used in sleep state estimation at a given ratio, in other words, when the count Mk is equal to or larger than a threshold m, the sleep state estimating unit 3 estimates in Step S202 the sleep state as the "wakeful state". For this epoch, the sleep state estimating unit 3 omits sleep state estimation that follows Step S104 and estimates in Step S108 the sleep state as the "wakeful state" before the process is returned to Step S101.

When Mk is smaller than m, on the other hand, the sleep state estimating unit 3 estimates that the subject is asleep and moves on to sleep state estimation from electrostatic capacity variations that are due to respiratory movement in steps subsequent to Step S104. In this case, the sleep state estimating unit 3 calculates the mean value of electrostatic capacity peak interval values (A), a coefficient of variation based on dispersion of the peak interval values (B), and a coefficient of variation based on dispersion of peak values (C) from respiratory movement variations within an epoch used in sleep state estimation as has been described above. The mean peak interval value A, the coefficient of variation B based on dispersion of the peak interval values, and the coefficient of variation C based on dispersion of the peak values are calculated from respiratory movement of all intervals including intervals where respiratory movement variations are larger than the body movement threshold.

Although inclusion of the intervals where respiratory movement variations are larger than the body movement threshold in calculation of the mean peak interval value A, the coefficient of variation B based on dispersion of the peak interval values, and the coefficient of variation C based on dispersion of the peak values makes the coefficients of variation B and C very large, it raises no particular processing problems since the sleep state can be judged correctly as explained below:

When the process proceeds from Step S104 to Step S105, the next step is Step S106 or Step 108 and either case the estimation result is the "wakeful state" or the "hypnagogic state". When the process proceeds to Step S109, the subsequent step is Step S112, where the "hypnagogic state" is given as the estimation result. When the process proceeds to Step S113, the subsequent step is Step S114, where "light sleep" is given as the estimation result. When the process proceeds to Step S117, the subsequent step is Step S120, where "light sleep" is given as the estimation result. Thus "deep sleep" is not given as the estimation result in any case and the process works fine.

Since the sleep state estimation device that uses the electrostatic capacity type sensor 5 is capable of estimating whether it is the "wakeful state" or the "asleep" state in addition to the sleep state estimation performed by the device that uses the respiratory band, there is a stronger possibility that the sleep estimation differences between FIGS. 6A and 6B, namely, the conflicting results on whether it is the "wakeful state" or not in the period from 10000 seconds to 15000 seconds and the period from 15000 seconds to 20000 seconds, are dissolved. In other words, the sleep state estimation according to the flow chart of FIG. 9 will more likely to judge the sleep state in the period from 10000 seconds to 15000 seconds and the period from 15000 seconds to 20000 seconds as the "wakeful state" as polysomography does.

In the processing flow of FIG. 9, the sleep state is estimated as the "wakeful state" in an epoch that has a given ratio of electrostatic capacity variations caused by body movement (an epoch where the count Mk is equal to or larger than the threshold m). Alternatively, the estimation result for this epoch may be a "frequent body movement state" or "possibly wakeful state". This is to avoid prematurely estimating the sleep state in an epoch where the variation count Mk is equal to or higher than the threshold as the "wakeful state", and instead to label it as a state where wakefulness is one of the possibilities, for body movement can happen either in deep sleep or light sleep.

The sleep state estimating unit 3 in the above embodiment samples voltage changes measured by the vital signs information processing unit 2 at a sampling frequency of 10 Hz to digitize the measurements, and calculates the mean value A of peak interval values, the coefficient of variation B based on the peak interval values, and the coefficient of variation C based on dispersion of peak values from the results of measuring the voltage for each 30-second epoch to estimate the sleep state from the obtained A, B and C. The sampling frequency and the epoch length can be modified suitably.

The sleep state estimation thresholds a, b and c, against which the mean peak interval value A, the coefficient of variation B and the coefficient of variation C are compared in sleep state estimation performed by the sleep state estimating unit 3, are set appropriately by statistically processing data obtained from plural subjects.

The processing flows shown in FIGS. 5 and 9 can be carried out by any computer CPU or memory or other LSIs in terms of hardware, and by a program loaded onto a memory or the like in terms of software. The function blocks showing the structure of the sleep state estimation device in FIG. 1 can of course take various forms, and may be made up solely of hardware or software, or may be a combination of hardware and software. It is also possible to obtain the function blocks by downloading a program which gives the corresponding functions onto a computer device such as a personal computer from a CD-ROM or other media or from Internet or other networks.

The above description on an embodiment of the present invention is not to limit the present invention. The embodiment of the present invention can suitably be modified in various ways within the scope of the technical concept of the present invention.

What is claimed is:

1. A sleep state estimation device for estimating a sleep state from a range of sleep states extending from wakefulness to deep sleep, comprising:
   vital signs information processing means for extracting respiratory signals from output signals of a vital signs information sensor; and
   sleep state estimating means for estimating the sleep state based on the respiratory signals outputted by the vital signs information processing means; wherein the sleep state estimating means includes:

peak calculating means for calculating respiratory signal peak values in a given period from the respiratory signals outputted by the vital signs information processing means; and peak interval calculating means for calculating respiratory signal peak intervals in the given period from the respiratory signals, and wherein the sleep state estimating means estimates the sleep state based on the peak values and from the peak intervals.

2. A sleep state estimation device for estimating a sleep state, comprising:

vital signs information processing means for extracting respiratory signals from output signals of a vital signs information sensor; and sleep state estimating means for estimating the sleep state based on the respiratory signals outputted by the vital signs information processing means;

wherein the sleep state estimating means includes:

peak calculating means for calculating respiratory signal peak values in a given period from the respiratory signals outputted by the vital signs information processing means; and peak interval calculating means for calculating respiratory signal peak intervals in the given period from the respiratory signals, and wherein the sleep state estimating means estimates the sleep state based on the peak values and from the peak intervals wherein the sleep state estimating means further includes:

first coefficient of variation calculating means for calculating, from the peak intervals obtained by the peak interval calculating means, a first coefficient of variation which is based on dispersion of the peak intervals; and second coefficient of variation calculating means for calculating, from the peak values obtained by the peak calculating means, a second coefficient of variation which is based on dispersion of the peak values, and wherein the sleep state estimating means estimates the sleep state by comparing the first coefficient of variation and the second coefficient of variation against given thresholds.

3. A sleep state estimation device for estimating a sleep state, comprising:

vital signs information processing means for extracting respiratory signals from output signals of a vital signs information sensor; and sleep state estimating means for estimating the sleep state based on the respiratory signals outputted by the vital signs information processing means;

wherein the sleep state estimating means includes:

peak calculating means for calculating respiratory signal peak values in a given period from the respiratory signals outputted by the vital signs information processing means; and peak interval calculating means for calculating respiratory signal peak intervals in the given period from the respiratory signals, and wherein the sleep state estimating means estimates the sleep state based on the peak values and from the peak intervals wherein the sleep state estimating means further includes:

mean peak interval calculating means for calculating, from the peak intervals obtained by the peak interval calculating means, a mean value of the peak intervals; and a coefficient of variation calculating means for calculating, from the peak values obtained by the peak calculating means, a coefficient of variation which is based on dispersion of the peak values, and wherein the sleep state estimating means estimates the sleep state by comparing the mean peak interval value and the coefficient of variation against given thresholds.

4. A sleep state estimation device for estimating a sleep state, comprising:

vital signs information processing means for extracting respiratory signals from output signals of a vital signs information sensor; and sleep state estimating means for estimating the sleep state based on the respiratory signals outputted by the vital signs information processing means;

wherein the sleep state estimating means includes:

peak calculating means for calculating respiratory signal peak values in a given period from the respiratory signals outputted by the vital signs information processing means; and peak interval calculating means for calculating respiratory signal peak intervals in the given period from the respiratory signals, and wherein the sleep state estimating means estimates the sleep state based on the peak values and from the peak intervals wherein the sleep state estimating means further includes:

first coefficient of variation calculating means for calculating, from the peak intervals obtained by the peak interval calculating means, a first coefficient of variation which is based on dispersion of the peak intervals;

second coefficient of variation calculating means for calculating, from the peak values obtained by the peak calculating means, a second coefficient of variation which is based on dispersion of the peak values; and mean peak interval calculating means for calculating, from the peak intervals obtained by the peak interval calculating means, the mean value of the peak intervals, and wherein the sleep state estimating means estimates the sleep state by comparing the first coefficient of variation and the second coefficient of variation against given thresholds, and by comparing the mean peak interval value and the second coefficient of variation against given thresholds.

5. A sleep state estimation device according to any one of claims 1 through 4, further comprising:

wakeful state detecting means for detecting a wakeful state; and estimation aborting means for stopping, upon detection of the wakeful state by the wakeful state detecting means, sleep state estimation the sleep state estimating means is conducting.

6. A sleep state estimation device according to claim 5, wherein the wakeful state detecting means detects the wakeful state by extracting body movement signals from output signals of the vital signs information sensor.

7. A method for estimating a sleep state of an individual from a range of sleep state extending from wakefulness to deep sleep, the method comprising the steps of:
- a vital signs information processing step of extracting respiratory signals from output signals of a vital signs information sensor; and
- a sleep state estimating step of estimating a sleep state based on the respiratory signals extracted in the vital signs information processing step; wherein the sleep state estimating step includes:
  - a peak calculating step of calculating respiratory signal peak values in a given period from the respiratory signals extracted in the vital signs information processing step; and
  - a peak interval calculating step of calculating respiratory signal peak intervals in the given period from the respiratory signals, and
- wherein the sleep state is estimated based on the peak values and the peak intervals in the sleep state estimating step.

8. A method for estimating a sleep state comprising the steps of:
- a vital signs information processing step of extracting respiratory signals from output signals of a vital signs information sensor; and
- a sleep state estimating step of estimating a sleep state based on the respiratory signals extracted in the vital signs information processing step;
- wherein the sleep state estimating step includes:
  - a peak calculating step of calculating respiratory signal peak values in a given period from the respiratory signals extracted in the vital signs information processing step; and
  - a peak interval calculating step of calculating respiratory signal peak intervals in the given period from the respiratory signals, and
- wherein the sleep state is estimated based on the peak values and the peak intervals in the sleep state estimating step
- wherein the sleep state estimating step further includes:
  - a first coefficient of variation calculating step of calculating, from the peak intervals obtained in the peak interval calculating step, a first coefficient of variation which is based on dispersion of the peak intervals; and
  - a second coefficient of variation calculating step of calculating, from the peak values obtained in the peak calculating step, a second coefficient of variation which is based on dispersion of the peak values, and
- wherein the sleep state is estimated by comparing the first coefficient of variation and the second coefficient of variation against given thresholds in the sleep state estimating step.

9. A method for estimating a sleep state comprising the steps of:
- a vital signs information processing step of extracting respiratory signals from output signals of a vital signs information sensor; and
- a sleep state estimating step of estimating a sleep state based on the respiratory signals extracted in the vital signs information processing step;
- wherein the sleep state estimating step includes:
  - a peak calculating step of calculating respiratory signal peak values in a given period from the respiratory signals extracted in the vital signs information processing step; and
  - a peak interval calculating step of calculating respiratory signal peak intervals in the given period from the respiratory signals, and
- wherein the sleep state is estimated based on the peak values and the peak intervals in the sleep state estimating step
- wherein the sleep state estimating step further includes:
  - a mean peak interval calculating step of calculating, from the peak intervals obtained in the peak interval calculating step, a mean value of the peak intervals; and
  - a coefficient of variation calculating step of calculating, from the peak values obtained in the peak calculating step, a coefficient of variation which is based on dispersion of the peak values, and
- wherein the sleep state is estimated by comparing the mean peak interval value and the coefficient of variation against given thresholds in the sleep state estimating step.

10. A method for estimating a sleep state comprising the steps of:
- a vital signs information processing step of extracting respiratory signals from output signals of a vital signs information sensor; and
- a sleep state estimating step of estimating a sleep state based on the respiratory signals extracted in the vital signs information processing step;
- wherein the sleep state estimating step includes:
  - a peak calculating step of calculating respiratory signal peak values in a given period from the respiratory signals extracted in the vital signs information processing step; and
  - a peak interval calculating step of calculating respiratory signal peak intervals in the given period from the respiratory signals, and
- wherein the sleep state is estimated based on the peak values and the peak intervals in the sleep state estimating step
- wherein the sleep state estimating step further includes:
  - a first coefficient of variation calculating step of calculating, from the peak intervals obtained in the peak interval calculating step, a first coefficient of variation which is based on dispersion of the peak intervals;
  - a second coefficient of variation calculating step of calculating, from the peak values obtained in the peak calculating step, a second coefficient of variation which is based on dispersion of the peak values; and
  - a mean peak interval calculating step of calculating, from the peak intervals obtained in the peak interval calculating step, the mean value of the peak intervals, and
- wherein the sleep state is estimated by comparing the first coefficient of variation and the second coefficient of variation against given thresholds and by comparing the mean peak interval value and the second coefficient of variation against given thresholds in the sleep state estimating step.

11. A method according to any one of claims 7 through 10, further comprising:

a wakeful state detecting step of detecting a wakeful state; and an estimation aborting step of stopping, upon detection of the wakeful state in the wakeful state detecting step, sleep state estimation conducted in the sleep state estimation step.

12. A method according to claim 11, wherein the wakeful state is detected by extracting body movement signals from output signals of the vital signs information sensor in the wakeful state detecting step.

* * * * *